(12) United States Patent
Wu et al.

(10) Patent No.: US 7,727,525 B2
(45) Date of Patent: Jun. 1, 2010

(54) ENGINEERED ANTI-CD20 ANTIBODY FRAGMENTS FOR IN VIVO TARGETING AND THERAPEUTICS

(75) Inventors: Anna M. Wu, Sherman Oaks, CA (US); Tove Olafsen, Sherman Oaks, CA (US); Andrew A. Raubitschek, San Marino, CA (US)

(73) Assignees: City of Hope, Duarte, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 11/741,253

(22) Filed: Apr. 27, 2007

(65) Prior Publication Data

US 2007/0280882 A1    Dec. 6, 2007

Related U.S. Application Data

(60) Provisional application No. 60/799,785, filed on May 11, 2006.

(51) Int. Cl.
 *A61K 51/10* (2006.01)
 *A61K 49/00* (2006.01)
 *A61K 39/395* (2006.01)

(52) U.S. Cl. .................. 424/133.1; 424/1.49; 424/9.1; 424/144.1; 424/155.1; 424/174.1; 424/173.1; 530/387.7; 530/388.7; 530/388.73; 530/388.8

(58) Field of Classification Search ............... None
See application file for complete search history.

(56) References Cited

U.S. PATENT DOCUMENTS

| | | | |
|---|---|---|---|
| 4,348,376 | A | 9/1982 | Goldenberg |
| 4,454,106 | A | 6/1984 | Gansow et al. |
| 4,460,559 | A | 7/1984 | Goldenberg |
| 4,472,509 | A | 9/1984 | Gansow et al. |
| 4,676,980 | A | 6/1987 | Segal et al. |
| 4,816,567 | A | 3/1989 | Cabilly et al. |
| 4,831,175 | A | 5/1989 | Gansow et al. |
| 4,946,778 | A | 8/1990 | Ladner et al. |
| 5,091,513 | A | 2/1992 | Huston et al. |
| 5,260,203 | A | 11/1993 | Ladner et al. |
| 5,455,030 | A | 10/1995 | Ladner et al. |
| 5,518,889 | A | 5/1996 | Ladner et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,595,721 | A | 1/1997 | Kaminski et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,736,137 | A | 4/1998 | Anderson et al. |
| 5,843,398 | A | 12/1998 | Kaminski et al. |
| 5,856,456 | A | 1/1999 | Whitlow |
| 6,015,542 | A | 1/2000 | Kaminski et al. |
| 6,090,365 | A | 7/2000 | Kaminski et al. |
| 6,287,537 | B1 | 9/2001 | Kaminski et al. |
| 6,399,061 | B1 | 6/2002 | Anderson et al. |
| 6,455,043 | B1 | 9/2002 | Grillo-Lopez |
| 6,565,827 | B1 | 5/2003 | Kaminski et al. |
| 6,682,734 | B1 | 1/2004 | Anderson et al. |
| 2003/0219433 | A1* | 11/2003 | Hansen et al. ........... 424/141.1 |

FOREIGN PATENT DOCUMENTS

| | | |
|---|---|---|
| WO | 91/00360 A1 | 1/1991 |
| WO | 92/00373 A1 | 1/1992 |
| WO | 93/08829 A1 | 5/1993 |

OTHER PUBLICATIONS

Perez et al., ChemBioChem, 5:261-264, 2004.*
Altschul, S.F. et al., "Basic Local Alignment Search Tool," J. Mol. Biol. 215:403-410 (1990).
Altschul, S.F. et al., "Gapped BLAST and PSI-BLAST: A New Generation of Protein Database Search Programs," Nucleic Acids Res. 25:3389-3402 (1997).
Angal, S. et al., "A Single Amino Acid Substitution Abolishes the Heterogeneity of Chimeric Mouse/Human (IgG4) Antibody," Mol. Immun. 30:105-108 (1993).
Bansinath, M. et al., "Chronic Administration of a Nitric Oxide Synthase Inhibitor, $N^\omega$-Nitro-L-Arginine, and Drug-Induced Increase in Cerebellar Cyclic GMP In Vivo," NeuroChem. Res. 18:1063-1066 (1993).
Bebbington, C.R. et al., "High-Level Expression of a Recombinant Antibody From Myeloma Cells Using a Glutamine Synthetase Gene as an Amplifiable Selectable Marker," Biotech. 10:169-175 (1992).
Bergman, Y. et al., "Characterization of a Carcinogen-Induced Murine B Lymphocyte Cell Line of C3H/eB Origin," Eur. J. Immunol. 7:413-417 (1977).
Bloom, J.W. et al., "Intrachain Disulfide Bond in the Core Hinge Region of Human IgG4," Protein Sci. 6:407-415 (1997).
Cockett, M.I. et al., "The Use of Engineered E1A Genes to Transactivate the hCMV-MIE Promoter in Permanent CHO Cell Lines," Nucleic Acid Res. 19:319-325 (1990).
Cole, S.P.C. et al., "The EBV-Hybridoma Technique and Its Application to Human Lung Cancer," Monoclonal Antibodies and Cancer Therapy, pp. 77-96 (1985).
Defrise, M. et al., "Exact and Approximate Rebinning Algorithms for 3-D PET Data," IEEE Trans. Med. Imaging 16:145-158 (1997).
Dikmen, Z.G. et al., "A New Diagnostic System in Cancer Research: Bioluminescent Imaging (BLI)," Turk J. Med. Sci. 35:65-70 (2005).
Fishwild, D.M. et al., "High-Avidity Human IgGκ Monoclonal Antibodies From a Novel Strain of Minilocus Transgenic Mice," Nat. Biotech. 14:845-851 (1996).
Flusberg, B.A. et al., "Fiber-Optic Fluorescence Imaging," Nature Methods 2:941-950 (2005).
Flusberg, B.A. et al., "In Vivo Brain Imaging Using a Portable 3.9 Gram Two-Photon Fluorescence Microendoscope," Optics Letters 30:2272-2274 (2005).

(Continued)

*Primary Examiner*—Ron Schwadron
(74) *Attorney, Agent, or Firm*—Perkins Coie LLP; Lauren Sliger

(57) ABSTRACT

The present invention provides anti-CD20 antibody fragments for use as in vivo imaging probes and as therapeutic moieties for the diagnosis and treatment of NHL.

5 Claims, 6 Drawing Sheets

OTHER PUBLICATIONS

Fraker, P.J. et al., "Protein and Cell Membrane Iodinations with a Sparingly Soluble Chloroamide, 1,3,4,6-Tetrachloro-3a,6a-Diphenylglycoluril," Biochem. & Biophys. Res. Commun. 80:849-857 (1978).

Funovics, M.A. et al., "Catheter-based In Vivo Imaging of Enzyme Activity and Gene Expression: Feasibility Study in Mice," Radiology 231:659-666 (2004).

Galfre, G. et al., "Preparation of Monoclonal Antibodies: Strategies and Procedures," Methods in Enzymology 73:3-46 (1981).

Greenwood, F.C. et al., "The Preparation of $^{131}$I-Labelled Human Growth Hormone of High Specific Radioactivity," Biochem. J. 89:114-123 (1963).

Gurfinkel, M. et al., "Near-Infrared Fluorescence Optical Imaging and Tomography," Disease Markers 19:107-121 (2004).

Henikoff, S. et al., "Amino Acid Substitution Matrices from Protein Blocks," Proc. Natl. Acad. Sci. USA 89:10915-10919 (1992).

Iwasaki, T. et al., "$N^G$-Nitro-L-Arginine Methyl Ester Inhibits Bone Metastasis After Modified Intracardiac Injection of Human Breast Cancer Cells in a Nude Mouse Model," Jpn. J. Cancer Res. 88:861-866 (1997).

Karlin, S. et al., "Applications and Statistics for Multiple High-Scoring Segments in Molecular Sequences," Proc. Natl. Acad. Sci. USA 90:5873-5877 (1993).

Kenanova, V. et al., "Tailoring the Pharmacokinetics and Positron Emission Tomography Imaging Properties of Anti-Carcinoembryonic Antigen Single-Chain Fv-Fc Antibody Fragments," Cancer Res. 65:622-631 (2005).

Kinahan, P.E. et al., "Analytic 3D Image Reconstruction Using All Detected Events," IEEE Transactions on Nulear Sci. 36:964-968 (1989).

Kohler, G. et al., "Continuous Cultures of Fused Cells Secreting Antibody of Predefined Specificity," Nature 256:495-497 (1975).

Kozbor, D. et al., "The Production of Monoclonal Antibodies from Human Lymphocytes," Immun. Today 4:72-79 (1983).

Lewis, M.R. et al., "An Improved Method for Conjugating Monoclonal Antibodies with N-Hydroxysulfosuccinimidyl DOTA," Bioconjugate Chem. 12:320-324 (2001).

Loening, A.M. et al., "AMIDE: A Free Software Tool for Multimodality Medical Image Analysis," Mol. Imaging 2:131-137 (2003).

Lonberg, N. et al., "Antigen-Specific Human Antibodies from Mice Comprising Four Distinct Genetic Modifications," Nature 368:856-859 (1994).

Lonberg, N. et al., "Human Antibodies from Transgenic Mice," Intern. Rev. Immunol. 13:65-93 (1995).

Magerstadt, M., "In Vitro Characterization of Therapeutic Radioimmunoconjugates," Antibody Conjugates and Malignant Disease 93-109 (1991).

Mahmood, U. et al., "Near-Infrared Optical Imaging of Protease Activity for Tumor Detection," Radiology 213:866-870 (1999).

Marks, J.D. et al., "By-Passing Immunization: Building High Affinity Human Antibodies by Chain Shuffling," Biotech. 10:779-783 (1992).

McCafferty, J. et al., "Phage Antibodies: Filamentous Phage Displaying Antibody Variable Domains," Nature 348:552-554 (1990).

Morrison, S.L., "Success in Specification," Nature 368:812-813 (1994).

Needleman, S.B. et al., "A General Method Applicable to the Search for Similarities in the Amino Acid Sequence of Two Proteins," J. Mol. Biol. 48:443-453 (1970).

Neuberger, M., "Generating High-Avidity Human Mabs in Mice," Nature Biotech. 14:826 (1996).

Olafsen, T. et al., "Characterization of Engineered Anti-p185$^{HER-2}$ (scFv-$C_H$3)$_2$ Antibody Fragments (Minibodies) for Tumor Targeting," Protein Eng. Des. Sel. 17:315-323 (2004).

Olafsen, T. et al., "Optimizing Radiolabeled Engineered Anti-p185$^{HER2}$ Antibdy Fragments for In Vivo Imaging," Cancer Res. 65:5907-5916 (2005).

Pearson, W.R. et al., "Improved Tools for Biological Sequence Comparison," Proc. Natl. Acad. Sci. USA 85:2444-2448 (1988).

Ramanujam, N. et al., "Fast and Noninvasive Fluorescence Imaging of Biological Tissues In Vivo Using a Flying-Spot Scanner," IEEE Trans. on Biomed. Eng. 48:1034-1041 (2001).

Schuurman, J. et al., "The Inter-Heavy Chain Disulfide Bonds of IgG4 are in Equilibrium with Intra-Chain Disulfide Bonds," Mol. Immun. 38:1-8 (2001).

Schwarze, S.R. et al., "In Vivo Protein Transduction: Delivery of a Biologically Active Protein into the Mouse," Science 285:1569-1572 (1999).

Siegel, J.A. et al., "Radioimmunotherapy Dose Estimation in Patients with B-Cell Lymphoma," Med. Phys. 20:579-582 (1993).

Smith, T.F. et al., "Comparison of Biosequences," Adv. Appl. Math. 2:482-489 (1981).

Stashenko, P. et al., "Characterization of a Human B Lymphocyte-Specific Antigen," J. Immunol. 125:1678-1685 (1980).

Stashenko, P. et al., "Expression of Cell Surface Markers After Human B Lymphocyte Activation," Proc. Natl. Acad. Sci. USA 78:3848-3852 (1981).

Sundaresan, G. et al., "$^{124}$I-Labeled Engineered Anti-CEA Minibodies and Diabodies Allow High-Contrast, Antigen-Specific Small-Animal PET Imaging of Xenografts in Athymic Mice," J. Nuclear Med. 44:1962-1969 (2003).

Suresh, M.R. et al., "Bispecific Monoclonal Antibodies from Hybrid Hybridomas," Methods in Enzymology 121:210-228 (1986).

Tabrizi-Fard, M.A. et al., "Pharmacokinetics, Plasma Protein Binding and Urinary Excretion of $N^\omega$-Nitro-L-Arginine in Rats," Br. J. Pharmacol. 111:394-396 (1994).

Traunecker, A. et al., "Bispecific Single Chain Molecules (Janusins) Target Cytotoxic Lymphocytes on HIV Infected Cells," EMBO J. 10:3655-3659 (1991).

Vassaux, G. et al., "In Vivo Noninvasive Imaging for Gene Therapy," J. Biomed. & Biotech. 2:92-101 (2003).

Whitlow, M. et al., "An Improved Linker for Single-Chain Fv with Reduced Aggregation and Enhanced Proteolytic Stability," Protein Eng. 6:989-995 (1993).

Yazaki, P.J. et al., "Humanization of the Anti-CEA T84.66 Antibody Based on Crystal Structure Data," Protein Eng. Des. Sel. 17:481-489 (2004).

Yazaki, P.J. et al., "Tumor Targeting of Radiometal Labeled Anti-CEA Recombinant T84.66 Diabody and T84.66 Minibody: Comparison to Radioiodinated Fragments," Bioconjugate Chem. 12:220-228 (2001).

* cited by examiner

FIGURE 1
*Signal peptide*
<u>ATG</u> GAT TTT CAG GTG CAG ATT ATC AGC TTC CTG CTA ATC AGT GCT TCA GTC ATA ATG
 M   D   F   Q   V   Q   I   I   S   F   L   L   I   S   A   S   V   I   M
                    $V_L$
TCC AGA GGA <u>CAA</u> ATT GTT CTC TCC CAG TCT CCA GCA ATC CTG TCT GCA TCT CCA GGG
 S   R   G   Q   I   V   L   S   Q   S   P   A   I   L   S   A   S   P   G GAG AAG GTC ACA ATG ACT TGC AGG GCC AGC TCA AGT GTA AGT TAC ATC CAC TGG TTC
 E   K   V   T   M   T   C   R   A   S   S   S   V   S   Y   I   H   W   F CAG CAG AAG CCA GGA TCA TCC CCC AAA CCC TGG ATT TAT GCC ACA TCC AAC CTG GCT
 Q   Q   K   P   G   S   S   P   K   P   W   I   Y   A   T   S   N   L   A TCT GGA GTC CCT GTT CGC TTC AGT GGC AGT GGG TCT GGG ACC TCT TAC TCT CTC ACA
 S   G   V   P   V   R   F   S   G   S   G   S   G   T   S   Y   S   L   T TGG AGC AGA GTG GAG GCT GAA GAT GCT GCC ACT TAT TAC TGC CAG CAG TGG ACT AGT
 I   S   R   V   E   A   E   D   A   A   T   Y   Y   C   Q   Q   W   T   S
                                                                *218 linker*
AAC CCA CCC ACG TTC GGA GGG GGG ACC AAG CTG GAA ATC AAA <u>GGC</u> TCC ACC TCT GGA
 N   P   P   T   F   G   G   G   T   K   L   E   I   K   G   S   T   S   G
                                                          $V_H$
TCC GGC AAG CCC GGA TCT GGC GAG GGA TCC ACC AAG GGC <u>CAG</u> GTA CAA CTG CAG CAG
 S   G   K   P   G   S   G   E   G   S   T   K   G   Q   V   Q   L   Q   Q CCT GGG GCT GAG CTG GTG AAG CCT GGG GCC TCA GTG AAG ATG TCC TGC AAG GCT TCT
 P   G   A   E   L   V   K   P   G   A   S   V   K   M   S   C   K   A   S GGC TAC ACA TTT ACC AGT TAC AAT ATG CAC TGG GTA AAA CAG ACA CCT GGT CGG GGC
 G   Y   T   F   T   S   Y   N   M   H   W   V   K   Q   T   P   G   R   G CTG GAA TGG ATT GGA GCT ATT TAT CCA GGA AAT GGT GAT ACT TCC TAC AAT CAG AAG
 L   E   W   I   G   A   I   Y   P   G   N   G   D   T   S   Y   N   Q   K TTC AAA GGC AAG GCC ACA TTG ACT GCA GAC AAA TCC TCC AGC ACA GCC TAC ATG CAG
 F   K   G   K   A   T   L   T   A   D   K   S   S   S   T   A   Y   M   Q CTC AGC AGC CTG ACA TCT GAG GAC TCT GCG GTC TAT TAC TGT GCA AGA TCG ACT TAC
 L   S   S   L   T   S   E   D   S   A   V   Y   Y   C   A   R   S   T   Y TAC GGC GGT GAC TGG TAC TTC AAT GTC TGG GGC GCA GGG ACC ACG GTC ACC GTC TCT
 Y   G   G   D   W   Y   F   N   V   W   G   A   G   T   T   V   T   V   S
    *Upper hinge*                    *Core*                    *Lower*
GCA <u>GAG</u> TCC AAA TAT GGG CCC CCA <u>TGC</u> CCA CCA TGC CCA <u>GCA</u> CCT GAG TTC CTG GGG
 A   E   S   K   Y   G   P   P   C   P   P   C   P   A   P   E   F   L   G
    $C_H3$
GGA CCA <u>GGG</u> CAG CCC CGA GAG CCA CAG GTG TAC ACC CTG CCC CCA TCC CAG GAG GAG
 G   P   G   Q   P   R   E   P   Q   V   Y   T   L   P   P   S   Q   E   E ATG ACC AAG AAC CAG GTC AGC CTG ACC TGC CTG GTC AAA GGC TTC TAC CCC AGC GAC
 M   T   K   N   Q   V   S   L   T   C   L   V   K   G   F   Y   P   S   D ATC GCC GTG GAG TGG GAG AGC AAT GGG CAG CCG GAG AAC AAC TAC AAG ACC ACG CCT
 I   A   V   E   W   E   S   N   G   Q   P   E   N   N   Y   K   T   T   P CCC GTG CTG GAC TCC GAC GGC TCC TTC TTC CTC TAC AGC AGG CTA ACC GTG GAC AAG
 P   V   L   D   S   D   G   S   F   F   L   Y   S   R   L   T   V   D   K AGC AGG TGG CAG GAG GGG AAT GTC TTC TCA TGC TCC GTG ATG CAT GAG GCT CTG CAC
 S   R   W   Q   E   G   N   V   F   S   C   S   V   M   H   E   A   L   H AAC CAC TAC ACA CAG AAG AGC CTC TCC CTG TCC CTA GGT AAA
 N   H   Y   T   Q   K   S   L   S   L   S   L   G   K FIG 2
A.
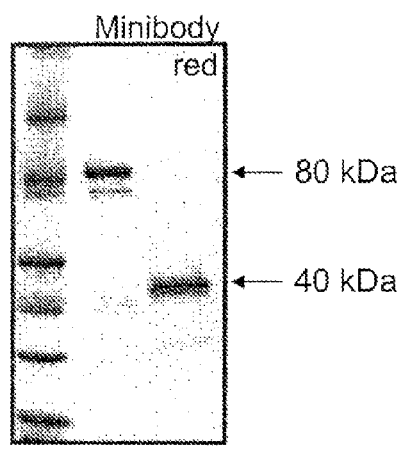
B.
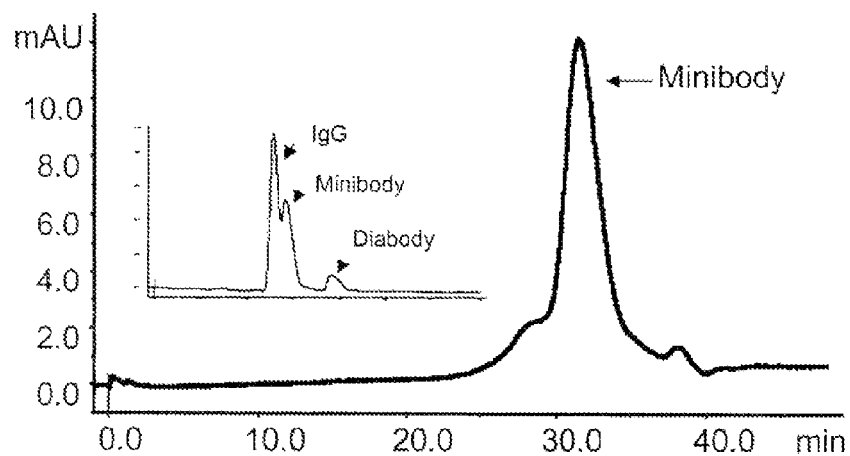
C.
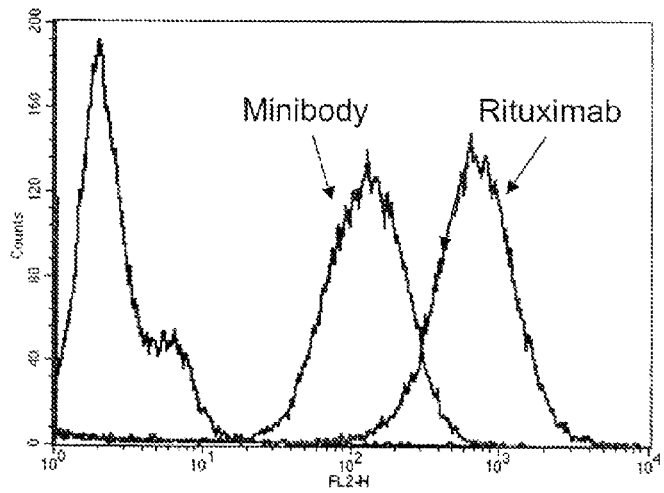

FIG 3
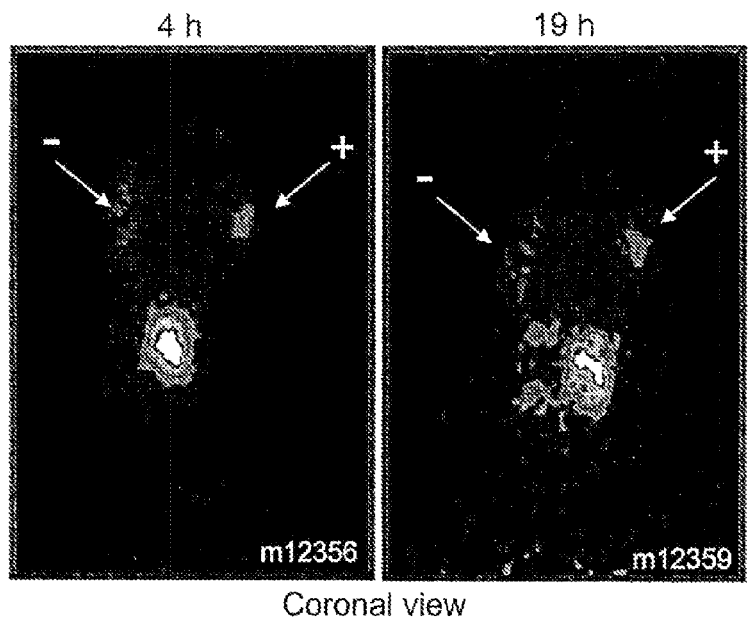
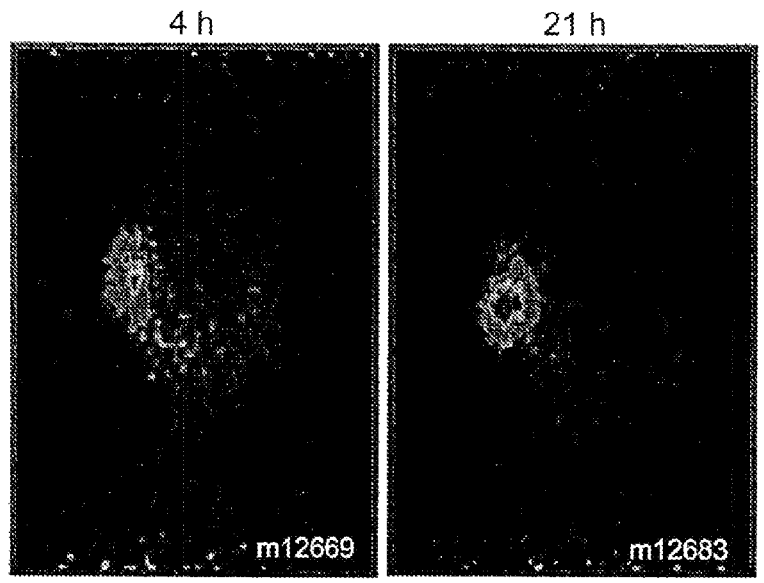

FIG 4

Anti-CD20 (rituximab) diabodies
(Theoretical pI/Mw: 9.04 /50.1 kDa)
Expression and Characterization

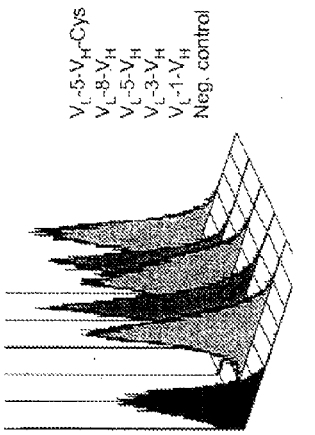

Diabody

Size exclusion (Superdex 75):

23.3 min (8)
23.7 min (5)
23.0 min (3)
23.4 min (1)

23.3 min (Cys-Db)

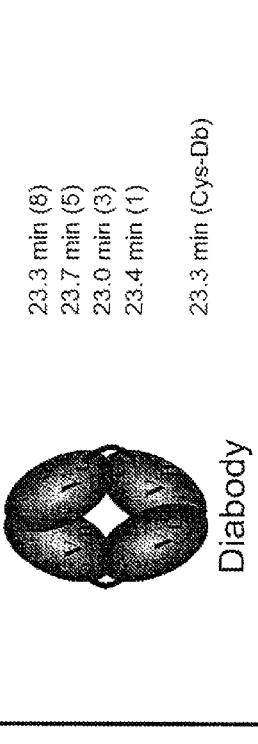

Several variants have been made:

1. $V_H$-8-$V_L$
   GGGSGGGG / VTVS
2. $V_L$-8-$V_H$, $V_L$-5-$V_H$, $V_L$-5-$V_H$-Cys, $V_L$-3-$V_H$, $V_L$-1-$V_H$
   GGGSGGGG / VTVS
   SGGGG / VTVS
   SGGGG / VTVSSGGC
   SGG / VTVS
   S / VTVS

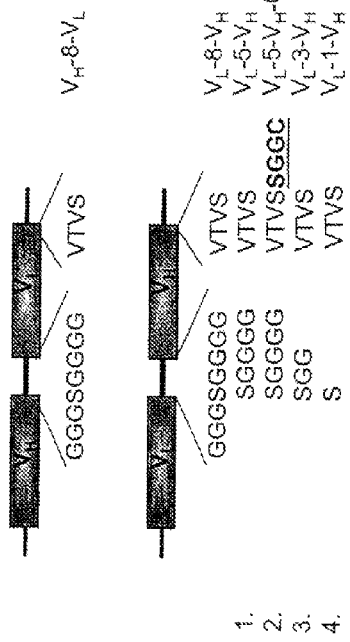

All $V_L$-$V_H$ variants elute at times corresponding to a dimer

Irr. Db / $V_H$-8-$V_L$ / $V_L$-8-$V_H$

Binding of $V_L$-$V_H$ diabody variants to CD20-positive cells by flow cytometry $V_L$-5-$V_H$-Cys
$V_L$-8-$V_H$
$V_L$-5-$V_H$
$V_L$-3-$V_H$
$V_L$-1-$V_H$
Neg. control

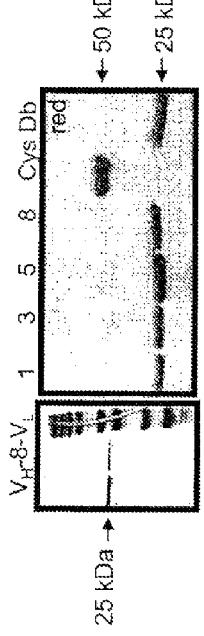

SDS-PAGE

SEQUENCE LISTING

<160> NUMBER OF SEQ ID NOS: 6

<210> SEQ ID NO 1
<211> LENGTH: 1182
<212> TYPE: DNA
<213> ORGANISM: Artificial Sequence
<220> FEATURE:
<223> OTHER INFORMATION: Anti CD-20 minibody

<400> SEQUENCE: 1

```
atggattttc aggtgcagat tatcagcttc ctgctaatca gtgcttcagt cataatgtcc      60
agaggacaaa ttgttctctc ccagtctcca gcaatcctgt ctgcatctcc aggggagaag     120
gtcacaatga cttgcagggc cagctcaagt gtaagttaca tccactggtt ccagcagaag     180
ccaggatcat cccccaaacc ctggatttat gccacatcca acctggcttc tggagtccct     240
gttcgcttca gtggcagtgg gtctgggacc tcttactctc tcacatggag cagagtggag     300
gctgaagatg ctgccactta ttactgccag cagtggacta gtaacccacc cacgttcgga     360
ggggggacca gctggaaat caaaggctcc acctctggat ccggcaagcc cggatctggc     420
gagggatcca ccaagggcca ggtacaactg cagcagcctg gggctgagct ggtgaagcct     480
ggggcctcag tgaagatgtc ctgcaaggct tctggctaca catttaccag ttacaatatg     540
cactgggtaa aacagacacc tggtcggggc ctggaatgga ttggagctat ttatccagga     600
aatggtgata cttcctacaa tcagaagttc aaaggcaagg ccacattgac tgcagacaaa     660
tcctccagca cagcctacat gcagctcagc agcctgacat ctgaggactc tgcggtctat     720
tactgtgcaa gatcgactta ctacggcggt gactggtact tcaatgtctg gggcgcaggg     780
accacggtca ccgtctctgc agagtccaaa tatgggcccc catgccacc atgcccagca     840 cctgagttcc tggggggacc agggcagccc cgagagccac aggtgtacac cctgccccca     900
tcccaggagg agatgaccaa gaaccaggtc agcctgacct gcctggtcaa aggcttctac     960
cccagcgaca tcgccgtgga gtgggagagc aatgggcagc cggagaacaa ctacaagacc    1020
```

```
acgcctcccg tgctggactc cgacggctcc ttcttcctct acagcaggct aaccgtggac   1080
aagagcaggt ggcaggaggg gaatgtcttc tcatgctccg tgatgcatga ggctctgcac   1140
aaccactaca cacagaagag cctctccctg tccctaggta aa                     1182
```

<210> SEQ ID NO 2
<211> LENGTH: 394
<212> TYPE: PRT
<213> ORGANISM: Artificial Sequence
<220> FEATURE:
<223> OTHER INFORMATION: Anti-CD20 minibody

<400> SEQUENCE: 2

```
Met Asp Phe Gln Val Gln Ile Ile Ser Phe Leu Leu Ile Ser Ala Ser
1               5                   10                  15

Val Ile Met Ser Arg Gly Gln Ile Val Leu Ser Gln Ser Pro Ala Ile
            20                  25                  30

Leu Ser Ala Ser Pro Gly Glu Lys Val Thr Met Thr Cys Arg Ala Ser
        35                  40                  45

Ser Ser Val Ser Tyr Ile His Trp Phe Gln Gln Lys Pro Gly Ser Ser
    50                  55                  60

Pro Lys Pro Trp Ile Tyr Ala Thr Ser Asn Leu Ala Ser Gly Val Pro
65                  70                  75                  80

Val Arg Phe Ser Gly Ser Gly Ser Gly Thr Ser Tyr Ser Leu Thr Ile
                85                  90                  95

Ser Arg Val Glu Ala Glu Asp Ala Ala Thr Tyr Tyr Cys Gln Gln Trp
            100                 105                 110

Thr Ser Asn Pro Pro Thr Phe Gly Gly Gly Thr Lys Leu Glu Ile Lys
        115                 120                 125

Gly Ser Thr Ser Gly Ser Gly Lys Pro Gly Ser Gly Glu Gly Ser Thr
    130                 135                 140

Lys Gly Gln Val Gln Leu Gln Gln Pro Gly Ala Glu Leu Val Lys Pro
145                 150                 155                 160

Gly Ala Ser Val Lys Met Ser Cys Lys Ala Ser Gly Tyr Thr Phe Thr
                165                 170                 175

Ser Tyr Asn Met His Trp Val Lys Gln Thr Pro Gly Arg Gly Leu Glu
            180                 185                 190

Trp Ile Gly Ala Ile Tyr Pro Gly Asn Gly Asp Thr Ser Tyr Asn Gln
        195                 200                 205

Lys Phe Lys Gly Lys Ala Thr Leu Thr Ala Asp Lys Ser Ser Ser Thr
    210                 215                 220

Ala Tyr Met Gln Leu Ser Ser Leu Thr Ser Glu Asp Ser Ala Val Tyr
225                 230                 235                 240

Tyr Cys Ala Arg Ser Thr Tyr Tyr Gly Gly Asp Trp Tyr Phe Asn Val
                245                 250                 255

Trp Gly Ala Gly Thr Thr Val Thr Val Ser Ala Glu Ser Lys Tyr Gly
            260                 265                 270

Pro Pro Cys Pro Pro Cys Pro Ala Pro Glu Phe Leu Gly Gly Pro Gly
        275                 280                 285

Gln Pro Arg Glu Pro Gln Val Tyr Thr Leu Pro Pro Ser Gln Glu Glu
    290                 295                 300

Met Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335
```

-continued

Asn Tyr Lys Thr Thr Pro Pro Val Leu Asp Ser Asp Gly Ser Phe Phe
                340                 345                 350

Leu Tyr Ser Arg Leu Thr Val Asp Lys Ser Arg Trp Gln Glu Gly Asn
            355                 360                 365

Val Phe Ser Cys Ser Val Met His Glu Ala Leu His Asn His Tyr Thr
        370                 375                 380

Gln Lys Ser Leu Ser Leu Ser Leu Gly Lys
385                 390

<210> SEQ ID NO 3
<211> LENGTH: 24
<212> TYPE: PRT
<213> ORGANISM: Artificial Sequence
<220> FEATURE:
<223> OTHER INFORMATION: fragment of Anti-CD20 diabody

<400> SEQUENCE: 3

Gly Leu Tyr Gly Leu Tyr Gly Leu Tyr Ser Glu Arg Gly Leu Tyr Gly
1               5                   10                  15

Leu Tyr Gly Leu Tyr Gly Leu Tyr
            20

<210> SEQ ID NO 4
<211> LENGTH: 12
<212> TYPE: PRT
<213> ORGANISM: Artificial Sequence
<220> FEATURE:
<223> OTHER INFORMATION: fragment of Anti-CD20 diabody

<400> SEQUENCE: 4

Val Ala Leu Thr His Arg Val Ala Leu Ser Glu Arg
1               5                   10

<210> SEQ ID NO 5
<211> LENGTH: 15
<212> TYPE: PRT
<213> ORGANISM: Artificial Sequence
<220> FEATURE:
<223> OTHER INFORMATION: fragment of Anti-CD20 diabody

<400> SEQUENCE: 5

Ser Glu Arg Gly Leu Tyr Gly Leu Tyr Gly Leu Tyr Gly Leu Tyr
1               5                   10                  15

<210> SEQ ID NO 6
<211> LENGTH: 24
<212> TYPE: PRT
<213> ORGANISM: Artificial Sequence
<220> FEATURE:
<223> OTHER INFORMATION: fragment of Anti-CD20 diabody

<400> SEQUENCE: 6

Val Ala Leu Thr His Arg Val Ala Leu Ser Glu Arg Ser Glu Arg Gly
1               5                   10                  15

Leu Tyr Gly Leu Tyr Cys Tyr Ser
            20

ENGINEERED ANTI-CD20 ANTIBODY FRAGMENTS FOR IN VIVO TARGETING AND THERAPEUTICS

CROSS-REFERENCES TO RELATED APPLICATIONS

This application claims the benefit of U.S. Provisional Patent Application No. 60/799,785, filed May 11, 2006, which is incorporated herein by reference.

STATEMENT AS TO RIGHTS TO INVENTIONS MADE UNDER FEDERALLY SPONSORED RESEARCH OR DEVELOPMENT

This invention was made with Government support of Grant Nos. P01 CA43904 and P50 CA107399 awarded by NCI/NIH. The Government has certain rights in this invention.

BACKGROUND OF THE INVENTION

The majority of non-Hodgkins lymphomas (NHLs) are of B-cell origin and over 90% express the leukocyte antigen CD20. The chimeric anti-CD20 antibody C2B8 (Rituximab; RITUXAN®, IDEC Pharmaceuticals, San Diego, Calif.; Genentech, San Francisco, Calif.) has been extensively evaluated in patients with recurrent B-cell lymphomas and its efficacy has been proven in several clinical trials. The mechanism of action in vivo is still not clear and multiple hypotheses have been generated i.e. induction of apoptosis, antibody dependent cell-mediated cytotoxicity (ADCC), phagocytosis, complement mediated cell-lysis (CML) and cross-priming of CD8+ cytotoxic T-cells. The efficacy of anti-CD20 antibodies has been further enhanced by radiolabeling with therapeutic isotopes such as $^{131}$I (tositumomab and Iodine I 131 tositumomab; BEXXAR®) and $^{90}$Y (ibritumomab tiuxetan; ZEVALIN®).

We have previously generated engineered antibody fragments including diabodies (dimers of single-chain Fv; scFv; 55 kDa), minibodies (dimers of scFv-$C_H$3; 80 kDa) and scFv-Fc DM (dimer of single-chain Fv-Fc, 105 kDa) with pharmacokinetics optimized for imaging in vivo. MicroPET imaging using I-124- or Cu-64-labeled fragments targeting both carcinoembryonic antigen (CEA) and HER2 demonstrate rapid, high level tumor targeting and fast blood clearance in mice carrying human colon carcinoma or breast carcinoma xenografts have resulted in high contrast, antigen-specific images. Fluorodeoxyglucose F18, (2-deoxy-2-[18F]fluoro-D-glucose) ([F-18]-FDG tracer) is currently standard for clinical PET imaging, but for lymphomas utility can be limited in cases of indolent disease with low metabolic activity. An imaging agent directed against a cell-surface target could provide complementary information.

Here, we describe the generation of anti-CD20 rituximab minibody that demonstrates rapid, specific localization to CD20 expressing tumors in a murine model, and are promising as imaging agents for detection of indolent NHLs. Anti-CD20 antibody fragments are useful for in vivo imaging and therapy for CD20 expressing cancers such as NHL, as well as for other CD20 targeted therapies, such as those used to treat autoimmune disease (RA, SLE, Sjogren syndrome, cold autoimmune hemolytic anemia) and graft vs. host disease.

BRIEF SUMMARY OF THE INVENTION

Antibodies can be engineered to produce fragments with properties optimized for cancer targeting. Fragments such as scFv, diabodies(scFv dimers), minibodies (scFv-CH3 dimers) and scFv-Fc (scFv-CH2-CH3 dimers) can be produced that retain high affinity binding for their antigens, and exhibit a controlled spectrum of targeting, distribution, and clearance kinetics in vivo (FIG. 1). Engineered antibodies can be useful unmodified, as biotherapeutics, or they can be utilized for delivery of imaging or toxic agents such as radionuclides or drugs, in vivo.

The CD20 antigen, a membrane integral phosphor protein, expressed in over 90% of the patients with non-Hodgkins lymphoma (NHL), does not shed, down-modulate or internalize in response to antibody binding making it an ideal target. Anti-CD20 antibodies i.e. rituximab, ZEVALIN® (ibritumomab tiuxetan), and BEXXAR® (tositumomab and Iodine I 131 tositumomab) have been approved by FDA for the treatment of patients with NHL. Current imaging modalities of lymphomas have limitations and there is an unmet need for better agents.

This invention describes the generation of antibody fragments from, e.g., anti CD20 C2B8 (rituximab) antibodies. The fragments include scFvs, diabodies, minibodies and scFv-Fc fragments. The proteins are expressed by secretion from mammalian cells and purified using conventional or affinity chromatography methods. They retain specific binding for CD20 cells in culture. FIGS. 2 and 3 demonstrate characterization of purified anti-CD20 diabodies, minibody and scFv-Fc.

Anti-CD20 minibody and scFv-Fc were radiolabeled with the positron emitting radionuclide, I 124, and evaluated for tumor targeting in vivo in mice bearing murine B lymphoma xenografts transfected with human CD20 antigen (38C13-CD20+; FIG. 4). Both are highly promising as imaging agents. The microPET images demonstrate excellent antigen-specific localization to the CD20 expressing tumors, with minimal activity in non-expressing tumors and in normal murine tissues.

BRIEF DESCRIPTION OF THE DRAWINGS

FIG. 1. DNA sequence (SEQ ID NO:1) and translated protein sequence (SEQ ID NO:2) of anti-CD20 minibody. Also indicated (underlined) are the beginnings of the following protein segments: signal peptide (for mammalian secretion), light chain variable region (VL) from murine 2B8 antibody, the 8 amino acid inter-domain linker peptide (218 Whitlow), heavy chain variable region (VH) from murine 2B8 antibody, human IgG4 hinge sequence [upper, middle (core) and lower] and the human IgG4 CH3 domain.

FIG. 2. In vitro characterization of rituximab minibody. A) SDS-PAGE analysis of anti-CD20 minibody under non-reducing and reducing (red) conditions, showing the 80 kDa covalent dimer and the 40 kDa monomeric subunits, respectively. B) Size-exclusion HPLC of anti-CD20 minibody showing homogeneous peak at expected molecular size. C) Flow cytometry binding studies of anti-CD20 minibody and parental antibody (c2B8; rituximab) showing distinct staining of the cells relatively to the negative control.

FIG. 3. Serial microPET scans of immunocompetent C3H mice bearing 38C13-hCD20+ and 38C13 (murine B-lymphoma) xenografts. A) Mouse injected with Cu-64 labeled anti-CD20 DOTA-minibody. Coronal sections from 4 and 19 hour time point are shown. B) Mouse injected with I-124 labeled anti-CD20 minibody. Coronal sections from 4 and 21 hour time point are shown.

FIG. 4. FIG. 4 shows anti-CD20 diabodies; expression and characterization. Fragments of some of the anti-CD20 diabody variants are shown in FIG. 4, including GGGSGGGG (SEQ ID NO: 3), VTVS (SEQ ID NO: 4), SGGGG (SEQ ID NO: 5), and VTVSSGGC (SEQ ID NO: 6).

FIG. 5 shows anti-CD20 diabodies; expression and characterization.

FIG. 6 shows micro-PET using the anti-CD20 minibody and scFv-Fc DM.

DETAILED DESCRIPTION OF THE INVENTION

I. Introduction

Figure 5:
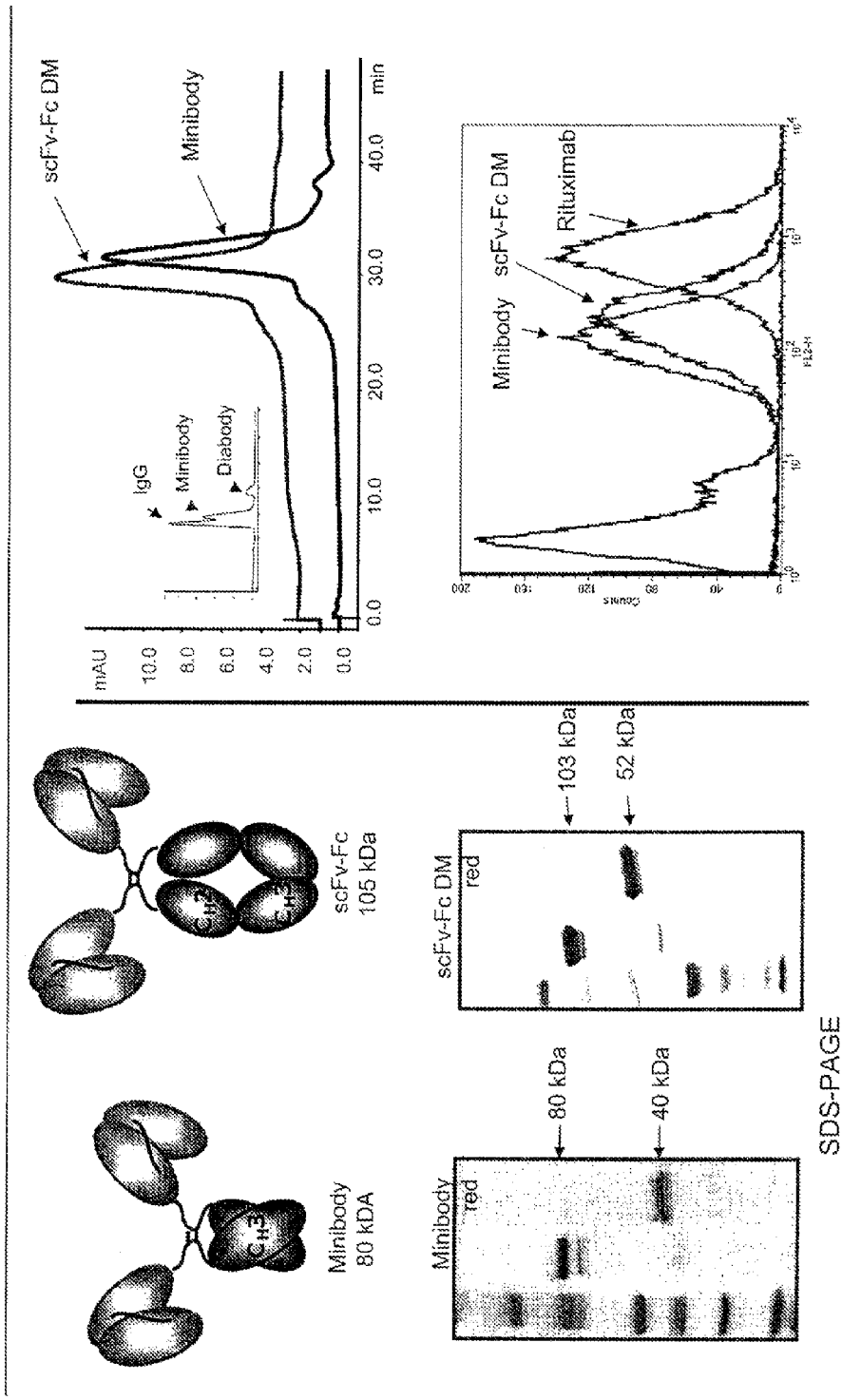
FIG. 5.
Figure 6:
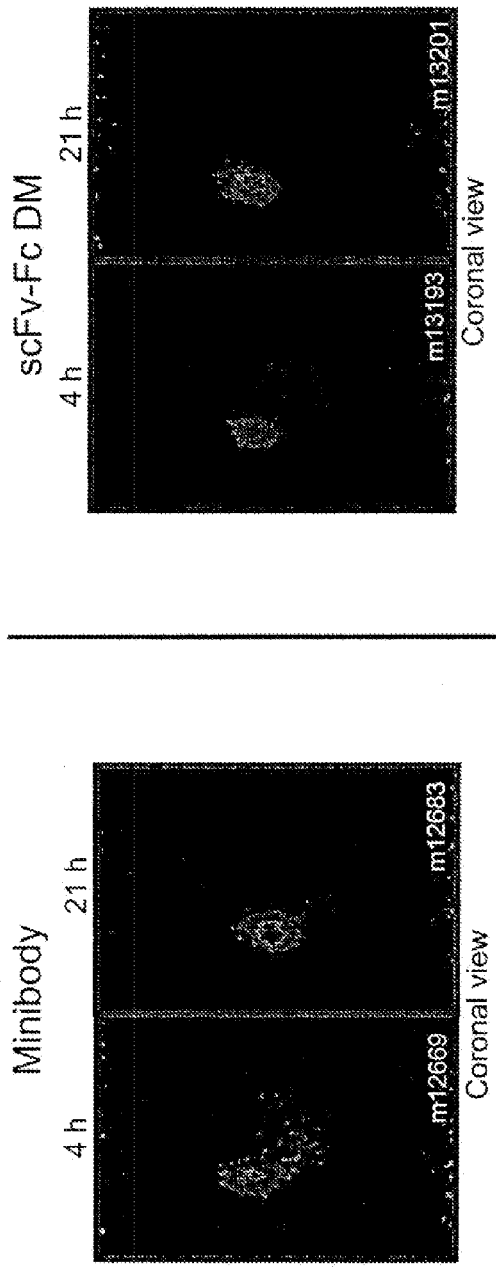
FIG. 6.

This invention focuses on detection of the leukocyte CD20 antigen, expressed in B-cell lymphomas, and utilizes genetically engineered antibody fragments that have been tailored specifically to optimize in vivo targeting, distribution and clearance.

The invention addresses the need for agents that have appropriate pharmacodynamic properties to target and image lymphomas that express CD20. There is a tremendous need in the field for effective agents to image cancers with sensitivity and specificity, particularly early stage tumors or ones with early metastasis not imageable by traditional means. The CD20 antigen is expressed in over 90% of the patients with non-Hodgkins lymphoma. Its expression is limited to the B-cell lineage from normal B-cell precursors through mature B-cells, but not by terminally differentiated plasma cells. This 33-37 kDa non-glycosylated, hydrophobic, phospho protein does not shed, down-modulate or internalize in response to antibody binding making it an ideal target. The current invention describes an innovative molecule with optimal characteristics for tumor imaging that may also have therapeutic utility by itself.

As above, the invention addresses the unmet need for imaging lymphoma, either early diagnosis or diagnosis of metastatic disease. Because lymphoma can involve almost any tissue in the body, the prognosis and management options of the disease are often determined by its anatomical extent (stage). Staging evaluation involves the use of a range of diagnostic modalities including structural (CT, X-ray, MRI, ultrasound, lymphography) and functional (bone, Ga-67, T1-201, peptide receptor radionuclide scanning) imaging as well as invasive procedures. All of these imaging modalities have significant limitations as stand-alone tests, which account for their frequent use in combination. PET imaging with 18F-FDG has been studied for staging, therapeutic monitoring and surveillance in patients with lymphoma. However, one major limitation is the radiotracer uptake especially in low-grade lymphomas with low metabolic activity. Another limitation is that since 18F-FDG is not a tumor-specific radiotracer, false-positive are frequently recorded due to active inflammatory lesions. An imaging agent targeting a surface molecule would therefore be useful in imaging patients with lymphomas.

There are multiple ways to make the invention. There are a variety of engineered antibody formats, such as svFv, diabodies, minibodies and scFv-Fc. In general, the agent should at least demonstrate bivalent, as opposed to monovalent binding. The overall size, shape and domain composition of the agent can be varied to suit the final application. Engineered fragments that exhibit optimal targeting in humans may be slightly different from formats that are optimal in mice. Since the final goal is human application, the invention incorporates a humanized set of antibody variable regions, as well as human hinge and constant regions. The proteins can be expressed in a variety of systems, including microbial, insect cells, mammalian cell culture and transgenic animals.

For imaging purposes, a variety of radionuclides can be attached to the engineered antibodies for detection with gamma or SPECT cameras, or PET scanners. For therapy one can attach drugs, toxins, cytokines, enzymes or other therapeutic moieties for CD20-targeted delivery to tumors. The engineered CD20-specific antibodies can be coupled to nanosensors for detection (in vitro and in vivo) or nanoparticles for delivery (in vivo). One can also incorporate the CD20 antibody fragments into viral vectors for targeted gene therapy of tumors. Anti-CD20 antibody fragments can be used alone or in combination with conventional therapies. In addition, the antibody can be used with T-cell receptors.

II. Definitions

The term "cancer" refers to human cancers and carcinomas, sarcomas, adenocarcinomas, lymphomas, leukemias, solid and lymphoid cancers, etc. Examples of different types of cancer include, but are not limited to, colorectal cancer, liver cancer (i.e., hepatocarcinoma), prostate cancer, renal cancer (i.e., renal cell carcinoma), bladder cancer, lung cancer (e.g., non-small cell lung cancer), breast cancer, thyroid cancer, pleural cancer, pancreatic cancer, ovarian cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, neuroblastoma, glioma, melanoma, B-cell lymphoma, Hodgkin's lymphoma, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma. In preferred embodiments, the methods of the present invention are useful for diagnosing, proving a prognosis for, and treating colorectal cancer, liver cancer, or a subtype thereof.

"Lymphomas" refer to Hodgkins lymphoma and non-Hodgkin's lymphoma (NHL), including B cell lymphomas such as chronic lymphocytic leukemia/small lymphocytic lymphoma, B-cell prolymphocytic leukemia, lymphoplasmacytic lymphoma/Waldenström macroglobulinemia, splenic marginal zone lymphoma, plasma cell neoplasms, plasma cell myeloma, plasmacytoma, monoclonal immunoglobulin deposition diseases, heavy chain diseases, extranodal marginal zone B cell lymphoma (MALT lymphoma), nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt lymphoma/leukemia, and lymphomatoid granulomatosis.

"Anti-CD20 antibody" refers to antibodies and fragments thereof that specifically bind to leukocyte CD20 antigen (see, e.g., Stashenko et al, *J. Immunol.* 125:1678-1685 (1980); Stashenko et al, *Proc. Natl. Acad. Sci. U.S.A.* 78:6 3848 (1981)). Such antibodies include fragments derived from the antibodies RITUAN® (rituximab), ZEVALIN® (ibritumomab tiuxetan), and BEXXAR® (tositumomab) (see, e.g., U.S. Pat. Nos. 5,595,721, 5,843,398, 6,015,542, 6,090,365, 6,565,827, 6,287,537 (BEXXAR®); U.S. Pat. Nos. 6,399, 061, 6,455,043, and 6,682,734 (ZEVALIN®); and U.S. Pat. No. 5,736,137 (RITUXAN®). Fragments include scFv, diabodies (scFv dimers), minibodies (scFv-$C_H3$ dimers), and scFv-Fc (scFv-$C_H2$-$C_H3$ dimers). Preferably the antibodies have bivalent binding, but can be monovalent. The antibodies are preferable humanized or human. They can be recombinantly expressed in microbes, insects, mammalian cells, plants, or transgenic mice and purified using conventional or affinity chromatography methods. They are optionally linked to radionuclides for in vivo imaging using gamma or SPECT cameras or PET scaners (e.g., $^{124}$I), or to toxins, drugs, cytokines, enzymes, or radionuclides ($^{131}$I, $^{90}$Y) for therapeutic applications. They can be optionally linked to nanosensors for detection or nanoparticles for delivery. The antibodies can be made using the sequences and methods described herein and in the literature cited herein.

By "therapeutically effective amount or dose" or "sufficient amount or dose" herein is meant a dose that produces effects for which it is administered. The exact dose will depend on the purpose of the treatment, and will be ascertainable by one skilled in the art using known techniques (see, e.g. Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof. The terms nucleic acid, "nucleic acid sequence", and "polynucleotide" are used interchangeably herein.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant nucleic acid" refers to a nucleic acid that was artificially constructed (e.g., formed by linking two naturally-occurring or synthetic nucleic acid fragments). This term also applies to nucleic acids that are produced by replication or transcription of a nucleic acid that was artificially constructed. A "recombinant polypeptide" is expressed by transcription of a recombinant nucleic acid (i.e., a nucleic acid that is not native to the cell or that has been modified from its naturally occurring form), followed by translation of the resulting transcript.

A "heterologous polynucleotide", "heterologous nucleic acid", "heterologous polypeptide" or "heterologous protein" as used herein, is one that originates from a source foreign to the particular host cell, or, if from the same source, is modified from its original form. Thus, a heterologous nucleic acid in a prokaryotic host cell includes a nucleic acid that is endogenous to the particular host cell but has been modified. Modification of the heterologous sequence may occur, e.g., by treating the DNA with a restriction enzyme to generate a DNA fragment that is capable of being operably linked to a promoter. Techniques such as site-directed mutagenesis are also useful for modifying a heterologous sequence.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g. a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" refers to material that is substantially or essentially free from components which interfere with the activity of an enzyme. For cells, saccharides, nucleic acids, and polypeptides of the invention, the term "isolated" refers to material that is substantially or essentially free from components which normally accompany the material as found in its native state. Typically, isolated saccharides, proteins or nucleic acids of the invention are at least about 50%, 55%, 60%, 65%, 70%, 75%, 80% or 85% pure, usually at least about 90%, 91%, 92%, 93%, 94%, 95%, 96%, 97%, 98%, or 99% pure as measured by band intensity on a silver stained gel or other method for determining purity. Purity or homogeneity can be indicated by a number of means well known in the art, such as polyacrylamide gel electrophoresis of a protein or nucleic acid sample, followed by visualization upon staining. For certain purposes high resolution will be needed and HPLC or a similar means for purification utilized. For oligonucleotides, or other sialylated products, purity can be determined using, e.g., thin layer chromatography, HPLC, or mass spectroscopy.

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80% or 85%, most preferably at least 90%, 91%, 92%, 93%, 94%, 95%, 96%, 97%, 98%, or 99% nucleotide or amino acid residue identity, when compared and aligned for maximum correspondence, as measured using one of the following sequence comparison algorithms or by visual inspection.

Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Nati. Acad. Sd. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to" or "specifically immunoreactive with", when referring to an antibody refers to a binding reaction which is determinative of the presence of the protein or other antigen in the presence of a heterogeneous population of proteins, saccharides, and other biologics. Thus, under designated immunoassay conditions, the specified antibodies bind preferentially to a particular antigen and do not bind in a significant amount to other molecules present in the sample. Specific binding to an antigen under such conditions requires an antibody that is selected for its specificity for a particular antigen. A variety of immunoassay formats can be used to select antibodies specifically immunoreactive with a particular antigen. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases, or as recombinant molecules. Thus, for example, pepsin digests an antibody below the disulfide linkages in the hinge region to produce F (ab)'$_2$, a dimer of Fab which itself is a light chain joined to $V_H$-$C_H$1 by a disulfide bond. The F (ab)'$_2$ may be reduced under mild conditions to break the disulfide linkage in the hinge region, thereby converting the F (ab)'$_2$ dimer into an Fab' monomer. The Fab' monomer is essentially Fab with part of the hinge region (see *Fundamental Immunology* (Paul ed., 3d ed. 1993). While various antibody fragments are defined above in terms of the digestion of an intact antibody, one of skill will appreciate that such fragments may be synthesized de novo either chemically or by using recombinant DNA methodology, e.g., scFv, scFv dimers, scFv-$C_{H3}$ dimers, and scFv-$C_H$2-$C_H$3 dimers. These methods are well known to those of skill in the art. Thus, the term antibody, as used herein, also includes antibody fragments either produced by the modification of whole antibodies, or those synthesized de novo using recombinant DNA methodologies (e.g., single chain Fv (scFv) scFv dimers, scFv-$C_H$3 dimers, and scFv-$C_H$2-$C_H$3 dimers) or those identified using phage display libraries (see, e.g., McCafferty et al., *Nature* 348:552-554 (1990)).

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g. Kuby, Immunology ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies, fragments, and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

In one embodiment, the antibody is conjugated to an "effector" moiety. The effector moiety can be any number of molecules, including labeling moieties such as radioactive labels or fluorescent labels for use in diagnostic assays, or therapeutic agents such as toxins, enxymes, drugs, cytokines, and radioactive moieties.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to IgE protein, polymorphic variants, alleles, orthologs, and conservatively modified variants, or splice variants, or portions thereof, can be selected to obtain only those polyclonal antibodies that are specifically immunoreactive with IgE proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

An "antigen" is a molecule that is recognized and bound by an antibody, e.g., peptides, carbohydrates, organic molecules, or more complex molecules such as glycolipids and glycoproteins. The part of the antigen that is the target of antibody binding is an antigenic determinant and a small functional group that corresponds to a single antigenic determinant is called a hapten.

A "label" is a composition detectable by spectroscopic, photochemical, biochemical, immunochemical, or chemical means. For example, useful labels include $^{32}$P, $^{125}$I, fluorescent dyes, electron-dense reagents, enzymes (e.g., as commonly used in an ELISA), biotin, digoxigenin, or haptens and proteins for which antibodies are available.

The term "immunoassay" is an assay that uses an antibody to specifically bind an antigen. The immunoassay is characterized by the use of specific binding properties of a particular antibody to isolate, target, and/or quantify the antigen.

"Biological sample" as used herein is a sample of biological tissue or fluid that contains nucleic acids or polypeptides. Such samples include, but are not limited to, tissue isolated from primates, e.g., humans, or rodents, e.g., mice, and rats. Biological samples may also include sections of tissues such as biopsy and autopsy samples, frozen sections taken for histologic purposes, blood, plasma, serum, sputum, stool, tears, mucus, hair, skin, bone cartilage, etc. Biological samples also include explants and primary and/or transformed cell cultures derived from patient tissues. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The term "pharmaceutically or physiologically acceptable carrier" is meant to include solvents and carriers that can be administered to a living subject, preferably those that maintain the tertiary and quaternary structure of the antibody of the composition.

As used herein, the term "administering" means intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g. intravenous, intramuscular, intra-arteriole, intradermal, subcutaneous, intraperitoneal, intraventricular, and intracranial. Other modes of delivery include, but are not limited to, the use of liposomal formulations, intravenous infusion, nanoparticles, etc.

By "co-administer" it is meant that a compound described herein is administered at the same time, just prior to, or just after the administration of one or more additional cancer therapies such as chemotherapy, hormonal therapy, radiotherapy, or immunotherapy.

"Radionuclides" for imaging/diagnostic uses or therapeutic uses are linked to the antibodies of the invention and include, but are not limited to, radionuclides such as $^{32}$P, $^{99}$Tc, $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, $^{123}$I, $^{124}$I, $^{131}$I and $^{212}$Bi.

For radiolabeling the antibody, there are several considerations for the method to be used. First, the radioisotope must be chosen, and then the means of attaching the radioisotope to the antibody must be selected. With respect to the choice of radioisotope, a general review of considerations is provided by Magerstadt (M. Magerstadt, Antibody Conjugates and Malignant Disease, pp. 93-109; c 1991 by CRC Press, Boca Raton, Fla). Principally one must consider the desired range of emission (affected by parameters including tissue type of the tumor, whether it is a solid or disseminated tumor and whether or not all tumor cells are expected to be antigen positive), the rate of energy release, the half-life of the isotope as compared to the infusion time and clearance rate, whether imaging or therapy is the aim of the labeled antibody administration, and the like. For imaging purposes, antibodies are labeled with a SPECT or PET detectable radionuclide such as $^{64}$Cu, $^{99}$Tc, $^{111}$In, $^{123}$I, $^{124}$I or $^{131}$I. For therapeutic purposes labeling with a beta-emitter, such as $^{90}$Y or $^{131}$I can be used. In some cases, labeling with an alpha-emitter or gamma-emitter is appropriate. Additional isotopes for therapeutic uses include $^{32}$P, $^{64}$Cu, $^{67}$Cu, $^{89}$Sr, $^{111}$In, $^{117m}$Sn, $^{153}$Sm, $^{177}$Lu, $^{186}$Re, and $^{188}$Re.

In considering the means for attaching the radioisotope to the antibody, one must consider first the nature of the isotope. Iodine isotopes can be attached to the antibody by a number of methods which covalently attach the isotope directly to the protein. Chloramine T labeling (Greenwood and Hunter, *Biochemistry Journal* 89:114 (1963)) and iodogen labeling (Fraker et al, *Biochem. Biophys. Res. Commun.*, 80:849 (1978)) are two commonly used methods of radioiodine labeling. For isotopes of metals, e.g. $^{90}$Y or $^{186}$Re, the isotope can be attached by covalently attaching a chelating moiety to the antibody and then allowing the chelator to coordinate the metal. Such methods are described, for example, by Gansow et al., U.S. Pat. Nos. 4,831,175, 4,454,106 and 4,472,509.

IV. In vivo Imaging

Those skilled in the art of visualizing the presence or expression of molecules including nucleic acids, polypeptides and other biochemicals in living patients will appreciate that the gene expression information described herein may be utilized in the context of a variety of visualization methods, e.g., gamma or SPECT cameras, or PET scanners. Such methods include, but are not limited to, single-photon emission-computed tomography (SPECT) and positron-emitting tomography (PET) methods. See, e.g., Vassaux and Grootwassink, "In Vivo Noninvasive Imaging for Gene Therapy," J. Biomedicine and Biotechnology, 2: 92-101 (2003); Turner, J., Smyth, P., Fallon, J. F., Kennedy, J. L., Potkin, S. G., FIRST BIRN (2006). Imaging and genetics in schizophrenia. Neuroinformatics, in press.

PET and SPECT imaging shows the chemical functioning of organs and tissues, while other imaging techniques—such as X-ray, CT and MRI—show structure. The use of PET and SPECT imaging is useful for qualifying and monitoring the development of NHL using anti-CD20 antibody fragments as described herein. In some instances, the use of PET or SPECT imaging allows diseases to be detected very early, or for metastasis to be detected early. This in vivo imaging is useful for staging and therapeutic monitoring.

After modification with appropriate tracer residues for PET or SPECT applications, the anti-CD20 antibodies of the invention are used to facilitate diagnosis of NHL as described herein. Similarly, labeled molecules which interact with the products of catalysis by the enzyme may be used for the in vivo imaging and diagnostic application described herein.

Various in vivo optical imaging techniques that are suitable for the visualization of fluorescent and/or enzymatic labels or markers include, but are not limited to, fluorescence microendoscopy (see, e.g., Flusberg et al., *Optics Lett.*, 30:2272-2274 (2005)), fiber-optic fluorescence imaging (see, e.g., Flusberg et al., *Nature Methods*, 2:941-950 (2005)), fluorescence imaging using a flying-spot scanner (see, e.g. Ramanujam et al., *IEEE Trans. Biomed. Eng.*, 48:1034-1041 (2001)), catheter-based imaging systems (see, e.g., Funovics et al., *Radiology*, 231:659-666 (2004)), near-infrared imaging systems (see, e.g. Mahmood et al., *Radiology*, 213:866-870 (1999)), fluorescence molecular tomography (see, e.g. Gurfinkel et al., *Dis. Markers*, 19:107-121 (2004)), and bioluminescent imaging (see, e.g., Dikmen et al., *Turk. J. Med. Sci.*, 35:65-70 (2005)).

Anti-CD20 antibodies, when conjugated to any of the above-described detectable moieties, can be administered in doses effective to achieve the desired image of CD20 positive cells in tumor tissue or cancerous cells in a subject. Such doses may vary widely, depending upon the particular detectable label employed, the type of tumor tissue or cancerous cells subjected to the imaging procedure, the imaging equipment being used, and the like. However, regardless of the detectable moiety or imaging technique used, such detection is aimed at determining where CD20 markers are concentrated in a subject, with such concentration being an indicator of the location of a tumor or tumor cells. Alternatively, such detection is aimed at determining the extent of tumor regression in a subject, with the size of the tumor being an indicator of the efficacy of cancer therapy.

IV. Pharmaceutical Compositions and Administration

Compounds of the invention can be administered directly to the patient for inhibition of cancer, tumor, or precancer cells in vivo. Administration is by any of the routes normally used for introducing a compound into ultimate contact with the tissue to be treated. The compounds are administered in any suitable manner, preferably with pharmaceutically acceptable carriers. Suitable methods of administering such compounds are available and well known to those of skill in the art, and, although more than one route can be used to administer a particular composition, a particular route can often provide a more immediate and more effective reaction than another route.

Methods of antibody administration are reviewed by Magerstadt (M. Magerstadt, *Antibody Conjugates and Malignant Disease*, pp. 93-109; c 1991 by CRC Press, Boca Raton, Fla). For treatment of lymphoma, it is considered on the one hand that intravenous injection is a good method, as the thoroughness of the circulation in rapidly distributing the labeled antibody is advantageous, especially with respect to avoiding a high local concentration of the radiolabel at the injection site. Intravenous administration is subject to limitation by a "vascular barrier", comprising endothelial cells of the vasculature and the subendothelial matrix. Yet, it is also noted that this barrier is a larger problem for uptake of labeled antibody by solid tumors. Lymphomas have relatively high blood flow rates, contributing to effective antibody delivery. In the case administration for the treatment of lymphoma, consideration should also be given to intralymphatic routes of administration, such as subcutaneous or intramuscular injection, or by catherization of lymphatic vessels. It is considered well-known to those of skill in the art how to formulate a proper composition of a labeled antibody for any of the aforementioned injection routes.

The timing of the administration can vary substantially. The entire dose can be provided in a single bolus. Alternatively, the dose can be provided by an extended infusion method or by repeated injections administered over a span of weeks. A preferable interval of time is six to twelve weeks between radioimmunotherapeutic doses. If low doses are used for radioimmunotherapy, the RIC could be administered at two week intervals. If the total therapeutic dose is fractionally delivered, it could be administered over a span of 2 to 4 days. Due to the lower dose infused, trace-labeled doses can be administered at short intervals; for clinical purposes, one to two week intervals are preferred.

Either or both the diagnostic and therapeutic administrations can be preceded by "pre-doses" of unlabeled antibody.

Goldenberg et al. describe radioimmunodiagnostic imaging and radioimmunotherapy of solid tumors (carcinomas) using an anti-carcinoembryonic antigen antibody. Many aspects of the materials and methods described by them in U.S. Pat. Nos. 4,348,376 and 4,460,559, can be applied as well to the present invention, which is directed to the diagnosis and therapy of lymphoma, a more disseminated tumor. Additional description of methods for estimating the radiometric dose received by a patient are provided in Siegel et al., *Med. Phys.* 20(pt. 2):579 (1993).

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17th ed. 1985)). For example, the methods described in Schwarze et al. (see *Science* 285:1569-1572 (1999)) can be used.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient, in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound or vector in a particular patient In determining the effective amount of the modulator to be administered in the treatment or prophylaxis of cancer, the physician evaluates circulating plasma levels of the therapeutic agent, toxicities, progression of the disease, and the production of antibodies. In general, the dose equivalent of a modulator is from about 1 ng/kg to 10 mg/kg for a typical patient. Administration of compounds is well known to those of skill in the art (see, e.g. Bansinath et al., *Neurochem Res.* 18:1063-1066 (1993); Iwasaki et al., *Jpn. J. Cancer Res.* 88:861-866 (1997); Tabrizi-Rad et al., *Br. J. Pharmacol.* 111: 394-396 (1994)).

For administration, modulators of the present invention can be administered at a rate determined by the LD-50 of the modulator, and the side-effects of the inhibitor at various concentrations, as applied to the mass and overall health of the patient. Administration can be accomplished via single or divided doses.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Example 1

Preparation of Anti-CD20 Antibody Fragments for in vivo Imaging and Therapy

Material and Methods

Design and Gene Assembly of Anti-CD20 Minibody

Splice overlap extension PCR (SOE-PCR) was used to create fully synthetic anti-CD20 variable (V) genes based on the V gene sequences of the murine 2B8. as described (Yazaki, P. J. et al., *Protein Eng Des Sel,* 17(5):481-9 (2004); Olafson, T. et al., *Cancer Res,* 65(13):5907-16 (2005)). Full-length 2B8 $V_L$ and $V_{11}$ chain genes were then assembled by SOE-PCR to produce the single chain Fv (scFv; Ladner et al., U.S. Pat. Nos. 4,946,778, 5,260,203, 5,455,030 and 5,518,889, and in Huston et al., U.S. Pat. No. 5,091,513) with the $V_L$-$V_H$ orientation joined by an 18 residue long linker [Whitlow 218 linker (GSTSGSGKPGSGEGSTKG)amino acids 129-146 of SEQ ID NO: 2 (Whitlow, M. et al., *Protein Eng,* 6(8):989 95 (1993)) U.S. patent application Ser. No. 08/224,591, filed Apr. 7, 1994 now U.S. Pat. No. 5,856,456]. The minibody was assembled by initial amplification of the human IgG4 hinge and $C_{11}3$ domain that were joined by SOE-PCR. The 2B8 scFv was then fused to $_{h-CH3\gamma4}$ by another SOE-PCR to produce a full length minibody construct with a scFv head-group. Following SOE-PCR which also included a signal peptide to the 5'-end (upstream) to enable secretion, the construct were cloned into pCR'-2.1-TOPO vector (Invitrogen Corp., Carlsbad, Calif.) and sequenced. In order to correct for the deficiency of IgG4 in forming inter-heavy-chain bonds (Angal, S. et al., *Mol Immunol,* 30(1):105-8 (1993); Bloom, J. W., et al., *Protein Sci,* 6(2):407-15 (1997); Schuurman, J. et al., *Mol Immunol,* 38(1):1-8 (2001)), a single mutation (S228P) was introduced in the core hinge region (CPSC; residues 226-229). The final sequence of the construct is shown in FIG. 1. Finally, the minibody was inserted into the mammalian expression vector pEE12 (Cockett, M. I. et al., Nucleic Acids Res, 19(2):319-25 (1991)) on Xbal and EcoRI sites. This vector contains the hCMV promoter and the glutamine synthtase gene for selection (Bebbington, C. R. et al., *Biotechnology (NY),* 10(2):169-75 (1992)).

Expression, Selection and Purification

A total of $2 \times 10^6$ NSO mouse myeloma cells (Galfre, G. et al., *Methods Enzymol,* 73(Pt B):3-46 (1981)) were transfected with 10 µg of linearized (cut with Sall) vector DNA by electroporation and selected in glutamine deficient media (JHR Biosciences, Lenexa, Kans.) (Bebbington, C. R. et al., *Biotechnology* (NY), 10(2):169-75 (1992)). Supernatants were screened for expression by ELISA and analyzed by Western blot for size as described (Olafson, T. et al., *Protein Eng Des Sel,* 17(4):315-23 (2004)). The minibody was captured by goat anti-human Fc specific antibodies and detected by alkaline phosphate (AP)-conjugated goat anti-human Fc specific antibodies (both from Jackson ImmunoResearch Labs., West Grove, Pa.). The highest producing clones were expanded and brought to terminal culture. Supernatants were passed over a protein L agarose (Pierce Biotechnology Inc., Rockford, Ill.) column, and bound proteins were eluted with 0.1 M Glycine into 10% v/v 2 M Tris base, pH 8.0. The eluted fractions containing the desired protein were dialysed against PBS using a molecular porous membrane tubing (mwco: 30K) and then concentrated down to 0.5-1.0 mL by Vivaspin 20 (mwco: 30K) (Vivascience AG, Hannover, Germany). The final concentration of purified protein was determined by A28o, using the extinction coefficients 1.4 mg/mL.

Biochemical Characterization of Purified Anti-CD20 Antibody Fragments

Aliquots of purified proteins were analyzed by SDS-PAGE under non-reducing or reducing (1 mM DTT) conditions (FIG. 2A). Samples were also subjected to size-exclusion high-pressure liquid chromatography (HPLC) on a Superdex 200 hr 10/30 column (GE Healthcare Bio-Sciences Corp., Piscataway, N.J.) using a 0.5 mL/minute flow rate and 50 mM $Na_3PO_4$/0.15 M NaCl (pH 7.0) buffer (FIG. 2B). Retention time was compared to standards of intact anti-CEA cT84.66 antibody, minibody and diabody as described (Kenanova, V. et al., Cancer Res, 65(2):622-31 (2005)).

Binding was assessed by indirect immunofluorescence using murine B-cell lymphoma 38C13 cells (Bergman, Y. et al., Eur J Immunol, 7(7):413-7 (1977)) transfected with human CD20 (FIG. 2C). Cells ($5 \times 10^5$) were incubated for 1 hour on ice with 500 μl minibody at 51 ifg/mL concentration in PBS/1% FBS. Cells were washed and stained with goat phycoerythrin (PE) conjugated anti-human Fc specific antibodies (Jackson ImmunoResearch) at 1:100 dilution. Rituximab (c2B8) was used as positive control.

Conjugation and Radiolabeling with $^{64}Cu$

Purified protein was conjugated to 1,4,7,10-tetraazacyclododecane-N.N',N'',N'''-tetraacetic acid (DOTA; Macrocyclics, Dallas, Tex.) by using the water-soluble N-hydroxysuccinimide method as described (Lewis, M. R. et al., Bioconjug Chem, 12(2):320-4 (2001); Yazaki, P. J. et al., Bioconjug Chem, 12(2):220-8 (2001)). The extent of modification was evaluated by isoelectric focusing.

The positron emitting isotope, $^{64}Cu$ (copper chloride in 0.1 M HCl; radionuclide purity>99%), was provided by Mallinckrodt Institute of Radiology (Washington University School of Medicine, St. Louis, Wash.). The anti-CD20 DOTA-conjugated minibody was labeled twice: 360 and 200 ug were incubated with 0.27 and 0.35 mCi, respectively, of "Cu in 0.1 M $NH_4$ citrate (p11 5.5) for 50 minutes at 43° C. Instant thin-layer chromatography using the Monoclonal Antibody ITLC Strips Kit (Biodex Medical Systems, Shirley, N.Y.) was used to determine the labeling efficiencies which were 88.5% and 65.4%.

Radioiodination with $^{124}I$

Purified rituximab minibody (0.2 mg) was radioiodinated with the positron emitting isotope $^{124}I$ (sodium iodide in 0.02 M NaOH; radionuclide purity>99%) provided by V. G. Khlopin Radium Institute & RITVERC GmbH (St. Petersburg, Russia) as previously described (Kenanova, V. et al., Cancer Res, 65(2):622-31 (2005)). The labeling efficiency was determined as described above. Immunoreactivity was assayed by incubating radioiodinated protein with an excess amount of 38C13-CD20+ cells for an hour, and spinning down the cells for counting of activity left in the supernatant. The minibody (100-150 μg) was radioiodinated with 0.60-0.72 mCu of $^{124}I$. The labeling efficiencies ranged from 65.5% to 82.2%, and the immunoreactivity was measured once to be 44.2%.

Animal Models

All animal handling was perfonrled in accordance with UCLA's Chancellor's Animal Research Committee guidelines. The human Burkitt lymphoma B-cell line, Daudi (CCL-213; American Type Culture Collection, Manassas, Va.) and the human adenocarcinoma cell line PC-3 (CRL-1435; ATCC) were propagated in RPMI/10% FBS supplemented with 1% 10,000 units/mL Penicillin-10,000 μg/mL Streptomycin-29.2 mg/mL Glutamine (Gibco; Invitrogen Corp., Grand Island, N.Y.). The murine B-lymphoma cell line, 38C13, was propagated in RPMI/10% FBS supplemented with 1% 10,000 units/mL Penicillin-10,000 μg/mL Streptomycin-29.2 mg/mL Glutamine and 0.2% 55 mM 2-mercaptoethanol (Gibco). Xenografts were established by s.c. injection of $0.5 \times 10^6$ cells on each shoulder region in mice as described (Olafson, T. et al., Protein Eng Des Sel, 17(4):315-23 (2004)). Daudi and PC-3 cells were resuspended in RPMI/matrigel (1:1) (Becton Dickinson Labware, Bedford, Mass.) prior to s.c. injection.

MicroPET Imaging

Mice were imaged using a Focus microPET scanner (Concorde Microsystems Inc., Knoxville, Tenn.). Acquisition time was 10 minutes (1 bed position), and images were reconstructed using a filtered backprojection (FBP) reconstruction algorithm (Kinahan, P. E. et al., IEEE Trans NS, 36(1):964-968 (1989); Defrise, M. et al., IEEE Trans Med Imaging, 16(2): 145-58 (1997)). After the last scan, tumors and organs were excised, weighed and counted in a Wallac WIZARD Automatic Gamma Counter (PerkinElmer Life and Analytical Sciences Inc., Wellesley, Mass.) and percentage of injected dose per gram (ID/g) was calculated. Images were displayed and regions of interest were drawn as described (Sundaresan, G. et al., J Nucl Med, 44(12):1962-1969 (2003)) and quantitated using AMIDE (Loening, A. M. et al., Mol Imaging, 2(3):131-7 (2003)). Regions of interest (ROIs) from a cylinder with known weight and radioactivity were used to determine a calibration factor (ItCi/voxel) for use in calculating % ID/g from the image ROIs.

Results

Expression and Characterization

Engineered anti-CD20 minibody was expressed at 4-10 μg/mL in terminal cultures of the mouse myeloma cell line NSO. Analysis of the purified protein on SDS-PAGE (FIG. 2A) demonstrated that the minibody migrated as a monomer consistent with its predicted MW of approximately 40 kDa under reducing conditions, and as a covalent dimer of approximately 80 kDa under non-reducing conditions. Size exclusion chromatography verified that the anti-CD20 minibody eluted at the time (31.6 min) corresponding to correctly folded dimer of expected molecular weight (FIG. 2B). The purity of the protein was determined from the size-exclusion chromatography to be above 95%. Binding to cellular target antigen was demonstrated by indirect immunofluorescence staining of 38C13-CD20+ cells incubated with purified protein using flow cytometry (FIG. 2C). The staining of rituximab is also shown.

MicroPET Imaging of Xenografts Using Anti-CD20$^{64}$Cu-DOTA-Minibody

To evaluate tumor targeting and normal organ uptake of the minibody, it was conjugated to DOTA and radiolabeled with $^{64}Cu$ and evaluated in two tumor systems; Daudi (human Burkitt's lymphoma) and 38013-CD20+ (mouse B-cell lymphoma) using PC-3 (human adenocarcinoma) and non-transfected 38C13 as antigen negative tumors.

MicroPET imaging was initially performed on nude animals with antigen positive Daudi tumors averaging 14 mg (range 10-21 mg) and PC-3 antigen negative tumors averaging 150 mg (range 72-252 mg). Mice were injected in the tail vein with 49-55 uCi of $^{64}Cu$-DOTA rituximab minibody (specific activity=0.66 uCi/ug) and whole body scan were obtained at 4 and ending at 21 hours after administration.

Following the last scan mice were sacrificed and tumors were excised and the % ID/g was calculated. The average uptake in the Daudi tumors (n=3) was 10.8(13.4) % ID/g (range 6.9-13.4% ID/g). Uptake by control PC-3 xenografts, liver and kidney (n=4) were 4.8(11.6), 5.9(±1.8) and 3.9(11.2) % ID/g respectively. The positive tumor to negative tumor ratio was 2.25.

In the above initial study the tumors were too small to show up in the image and for this reason a different animal model was employed. Here, three immunocompetent C3H mice were injected with 96-103 µCi of $^{64}$Cu-DOTA ritiximab minibody (specific activity=1.14 µCi/ug). Only one mouse developed a 38C18-CD20$^+$ tumor of 49 mg (FIG. 3A) and a two mice developed 38013 tumors of 96 and 106 mg. Mice were imaged and after the last scan (19 hours) sacrificed as described above in order to calculate % ID/g. In this model, the uptake in the 38C 13-CD20$^+$ tumor was 9.1% ID/g and the uptake by control 38C13 xenografts (n=2) was 4.7(117) % ID/g resulting in a ratio of 1.94. The activities in the liver and kidney (n=3) were higher than that seen in the animal model above; 12.2(13.4) and 21.8(12.5), respectively. Uptakes in spleen and lung (n=3) were 7.0(11.9) and 4.0(10.3) % ID/g respectively.

MicroPET Imaging of Xenografts Using Anti-CD20 $^{124I}$ Labeled Minibody

In order to evaluate tumor targeting of the minibody without the background activity as seen with $^{64}$Cu labeled minibody, 137-154 µCi $^{124}$I-labeled minibody (specific activity=3.14 µCi/ug) were injected into four immunocompetent C3H mice carrying 38C13-CD20$^+$ tumors averaging 611 mg (range 287-1000 mg) of which two carried 38C13 (674 and 1318 mg) xenografts. Whole body scan were obtained at 4 and ending at 21 hours after administration (FIG. 3B). Following the last scan mice were sacrificed and tumors were excised and the % ID/g was calculated. The average uptake in the CD20 positive tumors (n=4) was 7.3(±1.7) % ID/g (range 3.6-8.9% ID/g). Uptake by control 38C13 xenografts (n=2), liver. kidney and spleen were all below 1.0% ID/g, except lung which had 1.2% ID/g. Here, the positive tumor to negative tumor ratio was 8.95.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of diagnosing a CD20-expressing cancer in a human or mouse subject, the method comprising the steps of:
   a) administering to the subject an anti-CD20 antibody fragment comprising the amino acid sequence of SEQ ID NO: 2 linked to a detectable moiety; and
   b) detecting the moiety linked to the antibody fragment in the subject;
   wherein detection of the moiety diagnoses a CD20-expressing cancer in the subject.

2. The method of claim 1, wherein the cancer is a non-Hodgkin's lymphoma (NHL).

3. The method of claim 1, wherein the moiety linked to the antibody fragment is detected using PET or SPECT.

4. The method of claim 1, wherein the antibody fragment is further linked to a nanosensor.

5. The method of claim 1, the detectable moiety is 64Cu, 99Tc, 111In, 123I, 124I or 131I.

* * * * *

UNITED STATES PATENT AND TRADEMARK OFFICE
CERTIFICATE OF CORRECTION

PATENT NO. : 7,727,525 B2
APPLICATION NO. : 11/741253
DATED : June 1, 2010
INVENTOR(S) : Anna M. Wu et al.

It is certified that error appears in the above-identified patent and that said Letters Patent is hereby corrected as shown below:

Claim 5, line 7, insert --wherein-- before "the detectable moiety".

Signed and Sealed this

Twenty-sixth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,727,525 B2  Page 1 of 1
APPLICATION NO. : 11/741253
DATED : June 1, 2010
INVENTOR(S) : Anna M. Wu et al.

It is certified that error appears in the above-identified patent and that said Letters Patent is hereby corrected as shown below:

Claim 5, Column 26, line 7, insert --wherein-- before "the detectable moiety".

This certificate supersedes the Certificate of Correction issued October 26, 2010.

Signed and Sealed this

Twenty-third Day of November, 2010

David J. Kappos
*Director of the United States Patent and Trademark Office*